United States Patent [19]

Pfirmann et al.

[11] Patent Number: 5,468,863
[45] Date of Patent: Nov. 21, 1995

[54] PROCESS FOR THE PREPARATION OF SUBSTITUTED 2,3-DIFLUOROPYRIDINES

[75] Inventors: Ralf Pfirmann, Griesheim; Theodor Papenfuhs, Frankfurt am Main, both of Germany

[73] Assignee: Hoechst Aktiengesellschaft, Frankfurt, Germany

[21] Appl. No.: 19,096

[22] Filed: Feb. 18, 1993

[30] Foreign Application Priority Data

Feb. 20, 1992 [DE] Germany ............................ 42 05 170.3

[51] Int. Cl.$^6$ .................................................. C07D 211/38
[52] U.S. Cl. ............................ 546/345; 546/286; 546/287
[58] Field of Search ................................. 546/345, 286, 546/287

[56] References Cited

U.S. PATENT DOCUMENTS 4,822,887  4/1989  Little et al. ............................ 546/345

FOREIGN PATENT DOCUMENTS

| 0120575 | 3/1984 | European Pat. Off. . |
| 0104715 | 4/1984 | European Pat. Off. . |
| 0146924 | 7/1985 | European Pat. Off. . |
| 0192287 | 8/1986 | European Pat. Off. . |

OTHER PUBLICATIONS

S. Kumai,m et al, Chem. Abs. 117:233865k (1992) JP 04–164068.

*Primary Examiner*—C. Warren Ivy
*Assistant Examiner*—D. Margaret M. Mach
*Attorney, Agent, or Firm*—Connolly and Hutz

[57] ABSTRACT

The invention relates to a novel process for the preparation of substituted 2,3-difluoropyridines by reaction of substituted 2,3-halopyridines with fluoride salts in the presence of phase transfer catalysts, preferably in polar aprotic solvents, without removing the resulting substituted 2,3-difluoropyridines continuously from the reaction mixture. The substituted 2,3-difluoropyridines which can be prepared according to the invention are, inter alia, starting materials for the preparation of plant protection agents or pharmaceuticals.

21 Claims, No Drawings

PROCESS FOR THE PREPARATION OF SUBSTITUTED 2,3-DIFLUOROPYRIDINES

DESCRIPTION

The present invention relates to a novel process for the preparation of substituted 2,3-difluoropyridines, which are particularly important as starting materials for agrochemicals and pharmaceuticals.

In contrast to pyridines substituted by other activating groups, such as by trifluoromethyl, nitro or cyano groups (cf. EP Offenlegungsschrift 146,924), in 2,3,5-trichloropyridine, for example, the exchange of the chlorine atom in the 3-position only takes place with great difficulty, since the neighboring group effect, which is caused by the fluorine atom in the 2-position, is quite small.

The exchange of both chlorine atoms to give 5-chloro-2,3-difluoropyridine, as well as also in other substituted 2,3-dichloropyridines which, depending on reactivity, can greatly differ as a result of the particular substitution pattern, takes place in satisfactory yields, however, if the product is removed by distillation directly after its formation (semicontinuous procedure). In said EP Offenlegungsschrift 146,924, for reactivity reasons the reaction is carried out in the solvent dimethyl sulfoxide, which is industrially undesirable, but advantageous for the halex reaction, with simultaneous use of preferably pure cesium fluoride with continuous removal of the product by distillation. In spite of these reaction conditions, which are very favorable for this type of reaction, but uneconomical and ecologically questionable, only a yield of less than 55% of theory is nevertheless obtained (see the following Comparison Example 1; see also EP Offenlegungsschrift 146,924, Example 11). A process which could be carried out completely batchwise without continuous removal of the product by distillation would be industrially advantageous, however, because of the lower apparatus costs. Because of the low stability of the products under the reaction conditions and the low boiling point thereof, which can lead to sealing problems in the equipment used, until now continuous removal of the product just formed, as is described in EP Offenlegungsschrift 146,924, appears to be sensible and necessary.

If potassium fluoride is employed, even in a large excess, in sulfolane as a solvent, the yield (GC) of 5-chloro-2,3-difluoropyridine after 24 hours is only 5% of theory; the conversion about 50%. The reaction in which 5-chloro-2,3-difluoropyridine is formed thus progresses very slowly. Because of the low rate of formation, continuous removal by distillation is only carried out with difficulty. This is much easier in the case of more reactive substrates, such as, for example, 3-chloro-2-fluoro-5-trifluoromethylpyridine (see EP Offenlegungsschrift 146,924, Example 7), where, however, even here a simplification in terms of apparatus and an increased space yield without chemical yield impairment would be desirable.

If chlorine exchange is carried out in this reactive substrate, 3-chloro-2-fluoro-5-trifluoromethylpyridine, according to EP Offenlegungsschrift 104,725 without continuous removal by distillation, this requires the use of expensive cesium fluoride. Even using this reactive substrate and reactive fluoride, the yield is still not satisfactory (cf. this EP Offenlegungsschrift 104,715, Example 2: 48% of theory).

DE Offenlegungsschrift 3,700,764 furthermore discloses the preparation of 2,3-difluoro-5-chloropyridine via 2,5dichloropyridine by nitration of this product and reduction to 2,5-dichloro-3-aminopyridine, subsequent nitration to the nitramino derivative and treatment thereof by means of boron trifluoride etherate, 2,5-dichloro-3-fluoropyridine being obtained. This can be converted into the desired product by an exchange reaction with potassium fluoride and/or cesium fluoride. This very long route has, as disadvantages, inadequate yields, high toxicity and explosiveness of the intermediates and the use of the industrially undesirable reagent boron trifluoride.

The chlorine/fluorine exchange reaction with simultaneous denitrating fluorination of 2,5-dichloro-3-nitropyridine, which is also known from the literature (DE Offenlegungsschrift 3,700,779), also gives inadequate yields. In addition, the exchange of nitro groups is associated with problems in the reaction procedure (nitrous gases) and with significant proportions of side reactions, which can only be suppressed with difficulty. The use of expensive cesium chloride was therefore advisable until now.

According to EP Offenlegungsschrift 178,260, 2,3-difluoro-5-chloropyridine can be prepared starting from 2,5-dichloro-3-nitropyridine by hydrogenation of the nitro group, subsequent diazotization and exchange of the diazo group in hydrogen fluoride in a Monel autoclave and subsequent halex reaction with potassium fluoride and cesium fluoride (6:1) to introduce the fluorine atom in the 2-position. Better yields are obtained in this procedure, but this process also has many steps and is accompanied by corrosion problems in the handling of anhydrous hydrogen fluoride (uneconomical apparatus); additionally, it cannot compete economically with the introduction of both fluorine atoms in one step by means of inexpensive alkali metal fluoride.

It was therefore the object of the present invention to avoid the disadvantages of the prior art and in particular to make available a process for the preparation of substituted 2,3-difluoropyridines which is simple to carry out in terms of apparatus and manages without continuous removal of the prepared substituted 2,3-difluoropyridine by distillation, nevertheless gives satisfactory yields and high space yields with apparatus costs which are thus low and which avoids the use of large amounts of pure cesium fluoride.

To achieve this object, the invention proposes a process for the preparation of substituted 2,3-difluoropyridines, preferably 5-chloro-2,3-difluoropyridine, which comprises reacting substituted 2,3-dihalopyridines from the group comprising substituted 2,3-dichloropyridines, substituted 2-chloro-3-fluoropyridines and substituted 3-chloro-2-fluoropyridines with fluoride salts from the group comprising potassium fluoride, rubidium fluoride and tetraalkyl($C_1$–$C_{18}$)ammonium fluoride or mixtures thereof or mixtures of these fluorides individually or mixed with one another with cesium fluoride, the proportion of cesium fluoride in mixtures of this type being not more than 50% by weight, in the presence of phase transfer catalysts and preferably in polar aprotic solvents, without removing the substituted 2,3-difluoropyridines obtained in this process continuously from the reaction mixture.

The substituted 2,3-halopyridines employed in the process according to the invention are as a rule mono- or disubstituted, preferably monosubstituted. These substituted 2,3-halopyridines preferably have the formula (I)

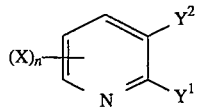

in which

X is halogen, preferably fluorine, chlorine or bromine or another electronegative radical, such as a cyano group or a trifluoromethyl radical, preferably the trifluoromethyl radical, $Y^1/Y^2$ independently of one another are fluorine or chlorine, where, however, both radicals are not simultaneously fluorine and n is 1 or 2, preferably 1.

According to the invention, those starting compounds (I) are in particular employed in which the radical X (if n =1) is in the 5- or 6-position. Examples of these are 2,3,5-trichloropyridine, 2,3,6-trichloropyridine, 2,3,5,6-tetrachloropyridine, 2,3-dichloro-5-trifluoromethylpyridine, 2,3-dichloro-5-cyanopyridine, 3,5-dichloro-2-fluoropyridine or 2,5-dichloro-3-fluoropyridine.

The preparation of these starting compounds is prior art. For instance, 2,3,5-trichloropyridine can be prepared in a known manner from chloral and acrylonitrile or from trichloroacetonitrile and acrolein with copper(I) catalysis (E. Steiner, P. Martin, D. Bellus, Helv. Chim. Acta, 65 (3) (1982), 983–985; SU Patent 1,583,416; SU Patent 1,182, 035). A further synthesis route is the chlorination of 3,5-dichloro-2-pyridone by means of phosphorus oxychloride (JP Offenlegungsschrift 54/059,283), the former being accessible, for example, either by chlorination of 6-hydroxynicotinic acid (EP Offenlegungsschrift 206,293) or in a multi-step process from 2-pyridone (JP Offenlegungsschrift 01/075,468) or from 2-aminopyridine by chlorination and boiling the diazo compound (JP Offenlegungsschrift 54/059, 283) or simple chlorination of 2-pyridone (Cava, Bhattacharyya, J. Org. Chem. 23 (1958) 1614).

2,3,6-Trichloropyridine is obtained, for example, in the chlorination of 2,6-dichloropyridine (EP Patent 239,904), in the treatment of pentachloropyridine with hydrazine in ethanol/triethylamine and sodium hydroxide solution (U.S. Pat. No. 3,947,457), and selectively in the reduction of pentachloropyridine with lithium aluminum hydride (F. Binns, S.M. Roberts, H. Suschitzky, J. Chem. Soc. C, (1970) (10), 1375–1380; J. Chem. Soc. D (1969) (20), 1211–1212). 2,3,5,6-Tetrachloropyridine can also be obtained in this way if less reductant is employed.

The 2,3-dichloro-5-trifluoromethylpyridine furthermore employed as a starting compound can be prepared from 2,2-dichloro-3,3,3-trifluoropropionaldehyde and acrylonitrile with copper(I) catalysis (U.S. Pat. No. 4,469,896). The reaction of 2,3-dichloro-5-trichloromethylpyridine with hydrogen fluoride (EP Patent 110,690) is also possible, where the trichloromethyl compound for its part can be prepared by chlorination of 2-chloro-5-trichloromethylpyridine by means of metal carbonyl catalysts (U.S. Pat. No. 4,331,811).

The substituted 2,3-difluoropyridines obtainable by the process according to the invention preferably have the formula (II)

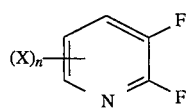

where X and n have the meaning as in the above formula (I). The compound here is preferably 5-chloro-2,3-difluoropyridine.

These substances are important starting materials for the preparation of agrochemicals and pharmaceuticals. For instance, 5-chloro-2,3-difluoropyridine can be used for the preparation of pyridinyloxyphenoxyalkanecarboxylic acid derivatives, which are herbicides with particularly advantageous properties (cf. EP Offenlegungsschriften 97,460; 142, 328; 248,968 and 296,518 and U.S. Pat. Nos. 4,750,931 and 4,935,051). The 2,3-difluoro-5-trifluoromethylpyridine obtainable according to the invention (cf. also EP Offenlegungsschrift 104,715) can be used, like 5-cyano-2,3-difluoropyridine, as a building block for active compounds contained in plant protection agents (EP Offenlegungsschrift 97,460). 2,3,6-Trifluoropyridine, which can be prepared according to the invention from compounds (I) where X=Cl (in this case triple chlorine exchange) or X=F (double chlorine exchange) and n=1, can be used as starting materials for antibacterial agents of the naphthyridinecarboxylic acid series (H. Koga, A. Itoh, S. Murayama, S. Suzue, T. Irikura, J. Med. Chem. 23 (1980), 1358; H. Egawa, T. Miyamoto, A. Minamida, Y. Nishimura, H. Okada, H. Uno, J. Matsumoto, J. Med. Chem. 27 (1984), 1543; EP Offenlegungsschrift 153,828 and EP Offenlegungsschrift 388, 298).

Suitable fluoride salts according to the invention are preferably potassium fluoride or tetraalkyl($C_1$–$C_{18}$)-ammonium fluoride and suitable mixtures with one another or with cesium fluoride, these mixtures with cesium fluoride containing not more than 50% by weight of cesium fluoride. Fluoride mixtures are preferably used which contain at least 75% by weight of potassium fluoride; mixtures of this type in particular consist of at least 90% by weight of potassium fluoride and at most 10% by weight of cesium fluoride. A mixture of 90% by weight potassium fluoride and 10% by weight cesium fluoride according to the invention (see examples) is designated as "potassium fluoride/cesium fluoride (9:1)" and a mixture of 60% by weight of potassium fluoride and 40% by weight of rubidium fluoride is called "potassium fluoride/rubidium fluoride (3:2)". In a further preferred embodiment, the fluoride salt used is only potassium fluoride.

About 0.9 to about 5, preferably between about 1 and about 2 and particularly preferably between about 1 and about 1.5, equivalents of fluoride salt are employed per chlorine atom to be exchanged.

The exchange reaction according to the invention is preferably carried out in polar aprotic solvents. Those which are suitable are, for example: sulfolane (tetramethylene sulfone), tetramethylene sulfoxide (TMSO), N,N-diethylacetamide, N,N-dimethylacetamide (DMAc), N,N-dimethylformamide (DMF), N-methylpyrrolidone (NMP), dimethyl sulfoxide (DMSO), dimethyl sulfone, diphenyl sulfoxide, diphenyl sulfone, tetramethylurea, tetra-nbutylurea, 1,3-dimethylimidazolidin-2-one (DMI) or mixtures of solvents of this type. Tetramethylene sulfone (sulfolane), N,N-dimethylacetamide (DMAc) and 1,3-dimethylimidazolidin-2-one (DMI) are preferably used; tetramethylene sulfone (sulfolane) and 1,3-dimethylimidazolidin-2-one (DMI) are particularly preferred.

The process according to the invention can also be carried out in other solvents. Those suitable for this purpose are non-polar solvents, such as, for example, benzonitrile, chloronaphthalenes, chlorobenzene, dichlorobenzenes, xylenes or toluene. Carrying out the reaction in the melt without addition of a solvent is also possible according to the invention.

The phase transfer catalysts used can be quaternary ammonium or phosphonium salts. Among suitable compounds, the following may be mentioned: tetraalkyl-($C_1$–$C_{18}$)-ammonium chlorides, bromides or fluorides, tetraalkyl-($C_1$–$C_{18}$)phosphonium chlorides or bromides, tetraphenylphosphonium chloride or bromide, and (phenyl)$_m$(alkyl-($C_1$–$C_{18}$))$_n$phosphonium chlorides or bromides, where m=1 to 3, n=3 to 1 and m+n=4. Mixtures of these salts can also be employed. With suitable choice of the catalyst for the particular compound to be reacted, which can easily be determined by a few routine tests, distinctly better space yields and chemical yields are obtained than by the process described in EP Offenlegungsschrift 146,924; additionally, the apparatus dead times and the total apparatus costs by the process according to the invention are significantly more favorable.

The amount of phase transfer catalyst is in general up to 20% by weight, preferably between 3 and 15% by weight and particularly preferably between 3 and 8% by weight, relative to the amounts of fluoride salt employed.

Phase transfer catalysts which can also be used are oligo- or polyalkylene glycol dimethyl ethers, where the alkylene radical contains 2 to 6 carbon atoms, preferably 2 and/or 3 carbon atoms, i.e. is preferably the ethylene and/or the propylene radical and in particular only the ethylene radical. The number of O-ethylene (glycol) units (—O—$CH_2$—$CH_2$—) and/or O-propylene units in these compounds can be from n=4 (for example tetraethylene glycol dimethyl ether) to about n=150; preferably, however, ethers are employed whose degree of polymerization is between n=4 and n=25. In the case of alkylene radicals having more than 3 carbon atoms, n is in general not higher than 6. The amount of these ethers employed, in particular glycol ethers, is for the most part between about 0.5% by weight and about 200% by weight, preferably between about 5 and about 100% by weight and particularly preferably between about 10 and about 50% by weight, relative to the amount of the fluoride salt employed. The particular advantage in the use of these compounds is that usually correspondingly less solvent can be used relative to the amount employed, since the glycol ether is in general liquid at the reaction temperature. Mixtures of these ethers with one another and mixtures of these ethers (individually or in a mixture) with the quaternary ammonium or phosphonium salts, preferably glycol ethers with quaternary phosphonium salts, can also be employed.

If the fluoride salts used are tetraalkyl($C_1$–$C_{18}$)ammonium fluorides, the addition of a further phase transfer catalyst is not necessary, since the fluoride salt itself is one of those which can thus be employed in stoichiometric and larger amounts.

The temperatures at which the reaction according to the invention takes place are expediently in the range from about 120° C. to about 250° C., preferably from about 170° C. to about 230° C. and particularly preferably from about 190° to 215° C. It is essential here that, according to the invention, the product obtained is not removed from the reaction mixture by distillation. After completion of the exchange reaction, which depending on the temperature used for the most part lasts for about 3 to about 20 hours, preferably about 5 to about 8 hours, the desired exchange product is separated from the unreacted starting product and from by-products, such as, for example, the mono- and, if necessary, the trifluorination product as well as possible isomerization products. As a rule, this is carried out by fractional distillation, the reaction salt in general first being separated off by filtration, then the filter cake being washed with an organic solvent and the mother liquor subsequently being fractionated. It is also practicable to remove the highly volatile constituents from the reaction mixture by distillation in order subsequently to subject the crude distillate obtained to a fine fractionation. The solvent in this procedure is separately recycled. In addition, an aqueous work-up is also possible, the product mixture being obtained from the water phase by extraction and purified by chromatographic methods. Particularly suitable extracting agents are non-polar organic solvents, such as, for example, cyclohexane or xylene (see also examples). Furthermore, melt crystallization can also be employed for purification.

When di(tri)chloro compounds are used, the process according to the invention can be carried out as one step or alternatively two steps. In the latter case, the di(tri)chloro compound concerned, for example 2,3,5-trichloropyridine, is first reacted to give the corresponding monofluoro compound and the reaction mixture obtained in this case is then subsequently reacted in a second step with further fluoride salts and, if appropriate, at elevated temperature compared to the first step without isolation of the monofluoro compound to give the desired di(tri)fluoro compound.

The process according to the invention proves to be particularly advantageous, since process engineering difficulties in industrial production, such as occur in alternative preparation processes, for example for 5-chloro-2,3-difluoropyridine, can be avoided. Material problems and complicated apparatus engineering may particularly be mentioned here. The multi-step nature of the synthesis is additionally avoided by this direct process. The use of spray-dried alkali metal fluoride in the process according to the invention in this case does partially shorten the reaction times, but is not absolutely necessary. The reaction can also be carried out with the addition of acid-binding agents, such as alkali metal and alkaline earth metal carbonates or basic oxides, such as, for example, magnesium oxide, or suitable mixtures. Potassium carbonate, which is used in amounts of about 1 to about 10% by weight, preferably from about 4 to about 6% by weight, relative to the amount of fluoride salt, is particularly preferred in this connection. The acid-binding agents are in general not essential for the progress of the reaction. In some cases, the reaction rate is significantly decreased by the formation of hydrogen fluoride during the reaction. In these cases, it is convenient, particularly also to avoid apparatus corrosion, to work in the presence of acid scavengers of this type. The use of these compounds during fractionation of the reaction mixture or of the crude products can be desirable on the grounds of corrosion in the fractionating plant, magnesium oxide being particularly preferred in this connection. For this purpose, up to about 10% by weight of acid scavenger, preferably between about 3 and 8% by weight, relative to the total amount of distillation bottom employed, is added to the fractionating still.

The process according to the invention can be carried out at reduced pressure, elevated pressure or atmospheric pressure. It is preferred to work at elevated pressure in order to avoid boiling of the reaction components, since under certain circumstances this can lead to losses which are not desirable for economical and occupational hygiene reasons.

Compared to known processes, particularly compared to processes which are carried out with removal of the product by distillation, the process according to the invention has substantial, surprising advantages. In the known processes a complicated open- and closed-loop control technology is necessary in order to ensure the uniform removal of the product by distillation without substantial amounts of intermediates which have to be additionally further reacted, but in spite of this a subsequent purifying fractionation is always additionally necessary. The distillation attachments to reaction apparatus primarily needed for this are in general not provided in installed plants. In addition, in the removal by distillation under reaction conditions hygiene problems can occur as a result of in some cases uncondensable, low-boiling constituents if the open- and closed-loop control units do not work completely reliably, which in the case of the substance class treated, however, is of great importance. During subsequent distillation, as in the process according to the invention, adequate purity of the product and of the fractions recycled in the next batch can be achieved, so that an altogether substantially simpler and, particularly as a result of only simple distillation, inexpensive work-up results. In order to ensure the stirrability of the reaction mixtures, large amounts of solvent are necessary, since a large part of the liquid components is removed from the mixture during the reaction and salts as well as mostly resinous by-products remain behind. The process according to the invention, as a result, furthermore has the advantage that it can be carried out using smaller amounts of solvent or, without solvent, in the melt, as a result of which the space yields and thus the capacity of the plants can be substantially increased. Due to the use of the phase transfer catalysts according to the invention, the extensive reaction additionally takes place without the use of large amounts of expensive cesium fluoride or of dimethyl sulfoxide and without substantial decomposition, as is known in processes known from the literature. Due to the distinctly lower proportions decomposed, there is a greatly declining amount of resinous and thus unknown by-products. As a result, in addition to economical advantages, ecological advantages are also achieved, since less material has to be incinerated or dumped. The possibility of reprocessing the reacted reaction salts is also simpler, since these are affected by fewer organic impurities. In the case of strongly contaminated salts, as are obtained from known processes (for example EP 46,942), the working up and reuse of the salts, according to the batch, was impossible. If solvents are used in the process according to the invention for technical reasons, in no case is the use of dimethyl sulfoxide necessary. This can only be used in exceptional cases because of the higher toxicity, skin permeability and highly annoying odor, particularly on thermal stress, in industrial application.

The following examples are intended to illustrate the process according to the invention without restricting it thereto.

Exemplary embodiments

In some examples, the progress of the reaction was monitored gas-chromatographically by calibration by means of an internal standard (inert under the reaction conditions). As a result, the amount of product formed which can be obtained by working up can be determined exactly at any desired time. These batches could be carried out on a relatively large scale without problems without addition of the internal standard with subsequent working up, generally better results such as shorter reaction times, higher space yields and better yields even being obtained due to improvement of the stirring conditions.

The reaction mixtures are generally worked up by filtration of the reaction salts, washing of the filter cake with an organic solvent and subsequent fractionation of the mother liquor. It is also practicable to remove the highly volatile constituents directly from the reaction mixture by distillation in order subsequently to subject the crude distillate obtained to a fine fractionation. The solvent is separately recycled in this procedure.

EXAMPLE 1 (COMPARISON EXAMPLE)

18.2 g (0.1 mol) of 2,3,5-trichloropyridine were added to a suspension of 13.9 g (0.24 mol; 20% excess) of potassium fluoride, 0.5 g of potassium carbonate and 1 g of pentamethylbenzene (internal standard) in 50 g of sulfolane in a 100 ml three-necked flask with good stirring (baffle elements), internal temperature control and intensive condenser, the mixture previously having been dried by azeotropic distillation (3 mm Hg, 140° C.). The mixture was heated at 200° C. for 24 h (reflux) and the composition after this time was as follows: 2,3,5-trichloropyridine: 11% of theory -chloro-2,3-difluoropyridine: 5% of theory (space yield: 0.5 g/l h; selectivity: 14%) 3,5-dichloro-2-fluoropyridine: 38% of theory 2,3,5-trifluoropyridine:<1% of theory The yields indicated were determined by calibration against the internal standard.

If the reaction was carried out with continuous removal by distillation, a total of 18% of theory of 5-chloro-2,3-difluoropyridine (space yield: 2.0 g/l h; selectivity: 40%), 30% of theory of 3,5-dichloro-2fluoropyridine and 10% of 2,3,5-trichloropyridine were obtained.

If pure cesium fluoride (0.28 mol; 40% excess) and DMSO as the solvent were employed (as described in EP Offenlegungsschrift 146,924, Example 11) and the reaction was carried out with continuous removal by distillation, 50.4% of theory of 5-chloro-2,3-difluoropyridine (space yield: 5.2 g/l 2h; selectivity: 67%) and 7.8% of theory of 3,5-dichloro-2-fluoropyridine were isolated.

EXAMPLE 2

The procedure was as in Example 1, but 14.9 g (0.24 mol of potassium fluoride/cesium fluoride (9:1) instead of potassium fluoride and 1.4 g (10% by weight, relative to the fluoride mixture) of tetraphenylphosphonium bromide as the phase transfer catalyst were employed, which was also subjected to azeotropic drying. The mixture was heated at 215° C. for 14 h (reflux); the composition after this time was as follows: 2,3,5-trichloropyridine: 2% of theory 5-chloro-2,3-difluoropyridine: 14% of theory (space yield: 3.2 g/l h; selectivity: 39%) 3,5-dichloro-2-fluoropyridine: 45% of theory 2,3,5-trifluoropyridine:<1% of theory The yields indicated were determined by calibration against the internal standard.

EXAMPLE 3

The reaction was carried out as in Example 2; 15.3 g (0.24 mol) of potassium fluoride/cesium fluoride (6:1) were employed as the fluoride source and 1.5 g of tetrabutylphosphonium bromide as the phase transfer catalyst. After a reaction time of 9 h at 215° C., the reaction mixture had the following composition: 2,3,5-trichloropyridine: < 1% of theory -chloro-2,3-difluoropyridine: 34% of theory (space yield: 12.0 g/l h; selectivity: 87%) 3,5-dichloro-2-fluoropyridine: 43% of theory 2,3,5-trifluoropyridine: 2% of theory The yields indicated were determined by calibration against the internal standard.

EXAMPLE 4

14.6 g (0.24 mol) of potassium fluoride/cesium fluoride (12:1) and 1.5 g of ethyltrioctylphosphonium bromide as the phase transfer catalyst were used analogously to Example 2. The reaction mixture was kept at 215° C. for 9 h and then analyzed by GC (internal standard): 2,3,5-trichloropyridine: about 1% of theory -chloro-2,3-difluoropyridine: 39% of theory (space yield: 13.9 g/l h; selectivity 92.5%) 3,5-dichloro-2-fluoropyridine: 40% of theory 2,3,5-trifluoropyridine: 1% of theory The yields indicated were determined by calibration against the internal standard.

EXAMPLE 5

1.5 g of tetraethylene glycol dimethyl ether and 14.9 g (0.24 mol) of potassium fluoride/cesium fluoride (9:1) were employed according to the procedure of Example 2; the reaction mixture was kept at 215° C. for 15 h. Its composition after this time was as follows: 2,3,5-trichloropyridine:<1% of theory 5-chloro-2,3-difluoropyridine: 24% of theory (space yield: 5.1 g/l h; selectivity: 70%) 3,5-dichloro-2-fluoropyridine: 48% of theory 2,3,5-trifluoropyridine: 4% of theory The yields indicated were determined by calibration against the internal standard.

EXAMPLE 6 (TWO-STEP PROCESS)

18.2 g (0.1 mol) of 2,3,5-trichloropyridine in 50 g of sulfolane were first reacted for 5 h at 200° C. with 7.0 g (0.12 mol) of potassium fluoride in the presence of 1.4 g of tetra-n-octylphosphonium bromide as the phase transfer catalyst. After this time, 73% of theory of 3,5-dichloro-2-fluoropyridine (selectivity: 83%) and 12% of theory of 2,3,5-trichloropyridine were found in the mixture. The salt present after cooling was filtered off with suction and washed with 10 g of warm sulfolane (azeotropically dried). The mother liquor was then treated with 7.8 g (0.12 mol) of vigorously dried potassium fluoride/cesium fluoride (5:1) and heated to 215° C. After a further 5 h, the mixture had the following composition (GC, internal standard): 2,3,5-trichloropyridine: about 2% of theory 5-chloro-2,3-difluoropyridine: 42% of theory (space yield: 10.5 g/l h; selectivity: 72%) 3,5-dichloro-2-fluoropyridine: 23% of theory 2,3,5-trifluoropyridine:<1% of theory The yields indicated were determined by calibration against the internal standard.

EXAMPLE 7

73.0 g (0.4 mol) of 2,3,5-trichloropyridine were added to a suspension of 59.4 g (0.96 mol) of potassium fluoride/cesium fluoride (9:1), 5.9 g of octadecyltrimethylammonium chloride, 2.0 g of potassium carbonate and 4 g of pentamethylbenzene (internal standard) in 50 g of N,N-dimethylacetamide, the mixture previously having been dried by azeotropic distillation (3 mm Hg, 140° C.). The mixture was heated at 190° C. for 11 h in a glass autoclave (reflux) and the composition after this time was as follows: 2,3,5-trichloropyridine:<1% of theory 5-chloro-2,3-difluoropyridine: 25% of theory (space yield: 11.3 g/l h; selectivity: 51%) 3,5-dichloro-2-fluoropyridine: 33% of theory 2,3,5-trifluoropyridine: about 1% of theory The yields indicated were determined by calibration against the internal standard.

EXAMPLE 8

850 g of sulfolane, 204.3 g (3.3 mol) of potassium fluoride/cesium fluoride (9:1), 7.5 g of potassium carbonate and 20.4 g of tetra-n-octylphosphonium bromide as the phase transfer catalyst were azeotropically dried by removal of about 100 g of sulfolane by distillation (170° C.). 273.5 g (1.5 mol) of 2,3,5-trichloropyridine were then added at 190° C. and the reaction mixture was heated to 215° C. After about 2 h reflux commenced. This was maintained for 20 h, and all the substance which boiled below 3 mm Hg/140° C. was then removed from the reaction mixture by distillation. A first fraction (15.8 g) which contained 14.2 g of 5-chloro-2,3-difluoropyridine and 1.3 g of 3,5-dichloro-2-fluoropyridine (determined by GC by means of internal standard) was obtained. The second fraction (168.0 g) contained 89.4 g of 5-chloro-2,3-difluoropyridine and 64.5 g of 3,5-dichloro-2-fluoropyridine and the third fraction (b.p.>130° C./4 mm Hg) contained 98.5 g (GC) of sulfolane. The fractions were purified by fractionation. The yield was 46% for 5-chloro-2,3-difluoropyridine and 27% for 3,5-dichloro-2-fluoropyridine (total 73%, isolated). The yield of 5-chloro-2,3-difluoropyridine was 63%, relative to reacted material. The amount of 3-chloro-2,5-difluoropyridine, which additionally was about 5% of the quantity of 5-chloro-2,3difluoropyridine, was not taken into account here. (Space yield with respect to 5-chloro-2,3-difluoropyridine: 4.7 g/l·h; selectivity: 82%).

EXAMPLE 9

36.4 g (0.2 mol) of 2,3,6-trichloropyridine and 1 g of pentamethylbenzene were added to a suspension of 18 g (0.3 mol) of potassium fluoride/cesium fluoride (9:1), 2.5 g of tetra-n-butylphosphonium bromide and 1 g of potassium carbonate in 150 g of sulfolane which was dried by azeotropic distillation. The mixture was heated at 215° C. for 14 h in a glass autoclave and the following mixture was obtained: 2,3,6-trichloropyridine: 38% of theory 3-chloro-2,6-difluoropyridine: 23% of theory 3,6-dichloro-2-fluoropyridine: about 2% of theory The yields indicated were determined by calibration against the internal standard.

EXAMPLE 10

A solution of 27.9 g (0.3 mol) of tetramethylammonium fluoride in 150 g of N,N-dimethylacetamide, which had previously been freed from water residues by removal of solvent by distillation, was treated with 1 g each of potassium carbonate and pentamethylbenzene. 43.2 g (0.2 mol) of 2,3-dichloro-5-trifluoromethylpYridine was then added and the mixture was heated at 160° C. for 10 h. After this time, it contained the following compounds: 2,3-difluoro-5-trifluoromethylpyridine: 65% of theory 2-fluoro-3-chloro-5-trifluoromethylpyridine: 9% of theory 2,3-dichloro-5-trifluoromethylpyridine:<1% of theory The yields indicated were determined by calibration against the internal standard.

EXAMPLE 11

86.4 g (0.4 mol of 2,3-dichloro-5-trifluoromethylpyridine were added to an azeotropically dried suspension of 50.3 g (0.84 mol) of potassium fluoride/cesium fluoride (20:1), 1.5 g of hexadecyltriethylphosphonium bromide and 1 g of potassium carbonate in 100 g of 1,3-dimethylimidazolidin-2-one (internal standard 1 g of pentamethylbenzene). The mixture was heated at 190° C. for 12 h in a glass autoclave and then analyzed by GC. 51.8 g (0.28 mol/71% of theory) of 2,3-dichloro-5-trifluoromethylpyridine and 5 g (25 mmol, 6% of theory) of 3-chloro- 2-fluoro-5-trifluoromethylpyridine were present in the mixture. These could be removed from the mixture by distillation and then purified by fractionation. The boiling point of the product was 116–117° C. at 760 mm Hg and the intermediate boiled at between 137° C. and 140° C. B.p. 74 (66)°C./125 (108) mbar (5-chloro-2,3-difluoropyridine) B.p. 96° C./79 mbar (3,5-dichloro-2-fluoropyridine) B.p. about 142° C./1013 mbar (3-chloro-2, 5-difluoropyridine)

5-Chloro-2,3-difluoropyridine:

$^1$H-NMR (CDCl$_3$, internal standard TMS): δ=7.61 (ddd, 1H, J=2.24 Hz (H-6), 7.89 Hz (F-2), 8.41 Hz (F-3), _H-4), 7.97 (dd, 1H, J = 2.24 Hz (H-4), 1.80 Hz (F-2), H-6)

$^{19}$F-NMR (CDCl$_3$, internal standard CFCl$_3$): δ=−88.80 (ddd, 1F, J=1.80 Hz (H-6), 7.89 Hz (H-4), 25.67 Hz (F-3), F-2) −136.51 (dd, iF, J=8.41 Hz (H-4), 25.67 Hz (F-2), F-3)

MS:m/e (%); 50 (4), 64 (25), 69 (7), 87 (8), 94 (4), 114 (63), 122 (7), 130 (1), 149 (M$^+$, 100), 151 (34)

3-Chloro-2,5-difluoropyridine:

$^{19}$F-NMR (CDCl$_3$, internal standard CFCl$_3$): δ=−75.63 (d, 1F, J=28.0 Hz (F-5), F-2), −129.9 (dd, iF, J=6.4 Hz (H-4), 28.0 Hz (F-2), F-5)

3,5-Dichloro-2-fluoropyridine:

$^1$H-NMR (CDCl$_3$, internal standard TMS):

δ=7.83 (dd, 1H, J=2.32 Hz (H-6), 7.63 Hz (H-6), 7.63 Hz (F-2), H-6) 8.07 (dd, 1H, J=2.32 Hz (H-4), 1.47 Hz (F-2) (F-2), H-6)

$^{19}$F-NMR (CDCl$_3$, internal standard CFCl$_3$):

δ=73.77 (dd, 1F, J=1.47 Hz (H-6), 7.63 Hz (H-4), F-2)

MS: m/e (%)=50 (8), 68 (14), 75 (5), 85 (6), 94 (8), 103 (13), 110 (13), 130 (63), 165 (M$^+$, 100), 167 (67), 169 (12)

EXAMPLE 12

271.9 g (4.68 mol) of potassium fluoride and 5.7 g of potassium carbonate were suspended in 990 g of sulfolane and 90 g of sulfolane were removed from the suspension by distillation in vacuo. 21.3 g (37.8 mmol) of tetra-n-octylphosphonium bromide and 328.4 g (1.8 mol) of 2,3,5-trichloropyridine were added to the mixture which remained. The mixture was heated with stirring in an autoclave (Hastelloy C4) at 205° C. for 6 h; the resulting pressure remained below 0.5 bar. After cooling, the low-boiling constituents up to pure sulfolane were removed from the reaction mixture by distillation and quantitatively investigated by GC against an internal standard (p-xylene). The low-boiling mixture (558 g) contained 130.9 g (0.876 mol, 40% of theory) of 5-chloro 2,3-difluoropyridine and 90.2 g (0.543 tool, 30.2% of theory) of 3,5-dichloro-2-fluoropyridine (space yield: 18.2 g/l·h, selectivity 92%). The bottom which remained was filtered from the salts, the salts were washed and the solvent was redistilled and employed again in the next batch.

EXAMPLE 13

The procedure was as in Example 12, but instead of 271.9 g (4.68 mol) of potassium fluoride, 254.7 g (4.38 mol) of potassium fluoride mixed with 45.0 g (0.296 mol) of cesium fluoride and instead of 21.3 g of tetra-n-octylphosphonium bromide, 28.4 g of this compound were employed. The other quantities used remained unchanged, as well as the reaction conditions (time, vessel) and the working up and analysis. 144.5 g (0.967 mol, 53.7% of theory) of 5-chloro-2,3-difluoropyridine and 70.2 g (0.423 mol, 23.5% of theory) of 3,5-dichloro- 2-fluoropyridine were obtained in the mixture of the low-boiling components (516.2 g) removed by distillation (space efficiency: 20.1 g/l·h, selectivity: 90%).

EXAMPLE 14

400 g of sulfolane, 1.9 g of potassium carbonate and 85.4 g of potassium fluoride/cesium fluoride (9:1) were mixed together and 100 g of sulfolane were removed by distillation at 170° C./30 mm Hg. 109.2 g (0.6 mol) of 2,3,5-trichloropyridine and 6.8 g (12 mmol) of tetra-n-octylphosphonium bromide were added to the mixture and it was heated at 200° C. for 6 h. The low-boiling constituents were removed from the mixture by distillation and the distillate was analyzed (GC, quantitative). 14.6 g (0.272 mol, 45.3% of theory) of 5-chloro- 2,3-difluoropyridine and 34.7 g (0.209 mol, 34.8% of theory) of 3,5-dichloro-2-fluoropyridine were present (space yield: 16.1 g/l·h, selectivity: 94%). The procedure for working up the remaining liquid was as in Example 12.

EXAMPLE 15 (COMPARISON EXAMPLE)

109.2 g (0.6 mol) of 2,3,5-trichloropyridine were reacted in 300 g of sulfolane at 205° C. for 6 h with 104.6 g (1.8 mol) of potassium fluoride in the presence of 1.9 g of potassium carbonate. The reaction mixture had been dried, as described in the previous examples, by azeotropic distillation. After removal of the low-boiling fractions by distillation, only 5.1 g (39.2 mmol, 5.7% of theory) could be detected in the distillate (227 g). 3,5-Dichloro-2-fluoropyridine (82.7 g, 0.499 mol, 83.1%) was present as the main constituent (space yield: 2.0 g/l·h, selectivity:>95%).

We claim:

1. A process for the preparation of a substituted 2,3-difluoropyridine, which comprises reacting, a substituted 2,3-dihalopyridine with a fluoride salt, wherein said substituted 2,3-dihalopyridine is a substituted 2,3-dichloropyridine, a substituted 2-chloro-3-fluoropyridine or a substituted 3-chloro-2-fluoropyridine, the fluoride salt being potassium fluoride, rubidium fluoride or tetraalkyl(C$_1$–C$_{18}$)ammonium fluoride or a mixture thereof or a mixture of these fluorides individually or mixed with one another with cesium fluoride, the proportion of cesium fluoride in any said mixture containing cesium fluoride being not more than 50% by weight, in the presence of a phase transfer catalyst, without removing resulting substituted 2,3-difluoropyridine continuously from the reaction mixture.

2. The process as claimed in claim 1, wherein the reaction is carried out in a polar aprotic solvent.

3. The process as claimed in claim 1, wherein the substituted 2,3-halopyridine has the formula (I)

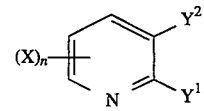

in which X is halogen or another electronegative radical, Y$^1$/Y$^2$ independently of one another are fluorine or chlorine, where, however, both radicals are not simultaneously fluorine and n is 1 or 2, preferably 1.

4. The process as claimed in claim 3, wherein the radical X, if n=1, is in the 5- or 6-position.

5. The process as claimed in claim 3, wherein a compound of said formula (I) is 2,3,5-trichloropyridine, 2,3,6-trichloropyridine, 2,3,5,6-tetrachloropyridine, 2,3-dichloro- 5-trifluoromethylpyridine, 2,3-dichloro-5-cyanopyridine, 3,5-dichloro-2-fluoropyridine, or 2,5-dichloro- 3-fluoropyridine.

6. The process as claimed in claim 1, wherein the fluoride salt used is potassium fluoride or tetraalkyl (C$_1$–C$_{18}$)ammonium fluoride or mixture with one another or with cesium fluoride, the amount of cesium fluoride in a said mixture being not more than 50% by weight.

7. The process as claimed in claim 1, wherein the fluoride salt used is potassium fluoride or a mixture of alkali metal fluorides which contains at least 90% by weight of potassium fluoride.

8. The process as claimed in claim 7, wherein the mixtures consist of at least 90% by weight of potassium fluoride and at most 10% by weight of cesium fluoride.

9. The process as claimed in claim 1, wherein the fluoride salt is employed in an amount corresponding to 0.9 to 5 equivalents, per chlorine atom to be exchanged.

10. The process as claimed in claim 1, wherein the phase transfer catalyst used is a quaternary ammonium or phosphonium compound, said quaternary ammonium or phosphonium compound being a tetraalkyl-($C_1$–$C_{18}$)ammonium chloride, bromide or fluoride, a tetraalkyl-($C_1$–$C_{18}$) phosphonium chloride or bromide, tetraphenylphosphonium chloride or bromide, or a (phenyl)$_m$-(alkyl($C_1$–$C_{18}$))$_n$phosphonium chloride or bromide, where m =1 to 3, n=3 to 1 and m+n=4.

11. The process as claimed in claim 10, wherein the phase transfer catalyst is employed in amounts up to 20% by weight, relative to the amount of alkali metal fluoride.

12. The process as claimed in claim 1, wherein the phase transfer catalyst employed is an oligo- or polyethylene glycol dimethyl ether which contains 4 to 150 glycol units (—O—$CH_2$—$CH_2$) or mixture thereof.

13. The process as claimed in claim 12, wherein the oligo- or polyethylene glycol diethyl ether is are used in amounts from 0.5 to 200% by weight, relative to the amount of fluoride salt.

14. The process as claimed in claim 2, wherein the polar aprotic solvent used is sulfolane (tetramethylene sulfone), tetramethylene sulfoxide (TMSO), N,N-diethylacetamide, N,N-dimethylacetamide (DMAc), N,N-dimethylformamide (DMF), N-methylpyrrolidone (NMP), dimethyl sulfoxide (DMSO), dimethyl sulfone, diphenyl sulfoxide, diphenyl sulfone, tetramethylurea, tetra-n-butylurea, 1,3-dimethylimidazolidin- 2-one (DMI) or mixture thereof.

15. The process as claimed in claim 1, wherein the reaction is carried out at temperatures between 120° C. and 250° C.

16. The process as claimed in claim 1 wherein the reaction is carried out in the presence of an acid-binding agent.

17. The process as claimed in claim 1, wherein the substituted 2,3-dihalopyridine is a substituted 2,3-dichloropyridine.

18. The process as claimed in claim 1, wherein, in a two-step process, a substituted 2,3-dichloropyridine is first reacted to give the substituted 2-fluoro- 3-chloropyridine and the crude mixture obtained in this reaction is reacted again with fluoride salt to give the desired 2,3-difluoropyridine.

19. A process for the preparation of a substituted 2,3-difluoropyridine, which comprises reacting the substituted 2,3-halopyridines of a formula (I)

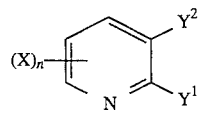

in which
X is halogen or another electronegative radical, $Y^1$/$Y^2$ independently of one another are fluorine or chlorine, where, however, both radicals are not simultaneously fluorine and n is 1 or 2, with a fluoride salt which is potassium, rubidium or tetraalkyl($C_1$–$C_{18}$)ammonium fluoride or a mixture with one another or a mixture of these fluorides individually or in a mixture with one another with cesium fluoride, the amount of cesium fluoride in said mixtures containing cesium fluoride being not more than 50% by weight, in a polar aprotic solvent and in the presence of a phase transfer catalyst which is a quaternary ammonium or phosphonium compound or an oligo- or polyethylene glycol dimethyl ether which contains 4 to 150 glycol units (—$OCH_2$—$CH_2$—), or mixtures thereof without removing the resulting substituted 2,3-difhoropyridines continuously from the reaction mixture.

20. A process for the preparation of a substituted 2,3-difhoropyridine, which comprises reacting a substituted 2,3-halopyridine of the formula (I)

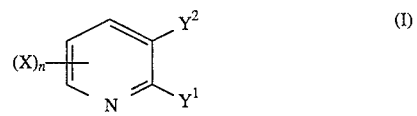

in which X is halogen or another electronegative radical, $Y^1$/$Y^2$ independently of one another are fluorine or chlorine, where, however, both radicals are not simultaneously fluorine and n is 1 or 2, with a fluoride salt which is potassium, rubidium or tetraalkyl($C_1$–$C_{18}$) ammonium fluoride or a mixture with one another or a mixture of these fluorides individually or in a mixture with one another with cesium fluoride, the amount of cesium fluoride in said mixtures containing cesium fluoride being not more than 50% by weight, in a polar aprotic solvent and in the presence of a phase transfer catalyst which is a quaternary ammonium or phosphonium compound or an oligo- or polyethylene glycol dimethyl ether which contains 4 to 150 glycol units (—$OCH_2$—$CH_2$—), or a mixture thereof without removing any resulting substituted 2,3-difluoropyridine continuously from the reaction mixtures, the reaction being carried out in two steps by first reacting the substituted 2,3-dichloropyridine to give the substituted 2-fluoro-3-chloropyridine and then converting the crude mixture obtained in this reaction into the desired 2,3-difluoropyridine using further fluoride salt.

21. The process as claimed in claim 1, wherein the reaction between the substituted 2,3-dihalopyridine starting material and the fluoride salt is first completed before separating any unreacted starting material and any by-products or isomerization products of said reaction from the desired substituted 2,3-difhoropyridine product.

* * * * *